US007809179B2

(12) United States Patent
Singh et al.

(10) Patent No.: US 7,809,179 B2
(45) Date of Patent: Oct. 5, 2010

(54) MANUFACTURING INSPECTION OF FOLDED FEMININE HYGIENE PRODUCTS BY CASCADING EDGE AND SKEW DETECTION

(75) Inventors: Rajesh Kumar Singh, Deerfield Township, OH (US); Thomas Keith Olschner, West Chester, OH (US); Ian James Semple, Kingston (CA); Paul Anthony Powell, Belleville (CA); Jeremy Georges Bertin, Fredericton (CA)

(73) Assignee: The Procter & Gamble Company, Cincinnati, OH (US)

( * ) Notice: Subject to any disclaimer, the term of this patent is extended or adjusted under 35 U.S.C. 154(b) by 1058 days.

(21) Appl. No.: 11/516,323

(22) Filed: Sep. 6, 2006

(65) Prior Publication Data
US 2007/0058840 A1    Mar. 15, 2007

Related U.S. Application Data

(60) Provisional application No. 60/715,513, filed on Sep. 9, 2005.

(51) Int. Cl.
*G06K 9/00* (2006.01)
*G06K 9/48* (2006.01)
*H04N 7/18* (2006.01)

(52) U.S. Cl. .............. 382/141; 382/199; 382/289; 348/92; 604/385.04

(58) Field of Classification Search ............ 382/141, 382/143, 152, 101, 102, 175, 199, 202, 203, 382/289, 291; 604/358–402, 385; 700/143; 356/429, 430, 432, 237, 239; 348/86, 88, 348/92–95; 250/559
See application file for complete search history.

(56) References Cited

U.S. PATENT DOCUMENTS 4,845,761 A * 7/1989 Cate et al. ............. 382/101
5,103,489 A * 4/1992 Miette ................... 382/101
5,359,525 A   10/1994 Weyenberg (Continued)

FOREIGN PATENT DOCUMENTS

WO    WO 01/76947 A1    10/2001

OTHER PUBLICATIONS

PCT International Search Report dated Feb. 22, 2007.

*Primary Examiner*—Brian P Werner
*Assistant Examiner*—Barry Drennan
(74) *Attorney, Agent, or Firm*—James E. Oehlenschlager; Roddy M. Bullock (57) ABSTRACT

A process is provided for inspecting an absorbent article constructed from multiple components. A filtered image is produced from the absorbent article. In the image of the absorbent article, a nonlinear first edge and a second edge are identified at a location where there is a course change in contrast. A center point and centerline of the absorbent article is calculated using the position of the first edge and the second edge. A skew of the absorbent article is calculated. These known locations are utilized to define at least one additional region of the image for further analysis. A third edge and fourth edge are identified at a location where there is a fine change in contrast. The skew of the third edge and the fourth edge within the defined region is calculated and compared to known parameters for the absorbent article.

15 Claims, 8 Drawing Sheets

U.S. PATENT DOCUMENTS

| | | | |
|---|---|---|---|
| 5,664,027 A * | 9/1997 | Ittner | 382/170 |
| 5,841,881 A * | 11/1998 | Iwakawa et al. | 382/101 |
| 5,977,501 A * | 11/1999 | Werkheiser et al. | 209/583 |
| 6,801,828 B2 * | 10/2004 | Popp et al. | 700/122 |
| 6,885,451 B2 | 4/2005 | Vogt et al. | |
| 6,888,143 B2 | 5/2005 | Vogt et al. | |
| 6,900,450 B2 | 5/2005 | Gimenez et al. | |
| 6,919,965 B2 | 7/2005 | Koele et al. | |
| 6,927,857 B2 | 8/2005 | Koele et al. | |
| 7,130,709 B2 * | 10/2006 | Popp et al. | 700/122 |
| 2005/0122531 A1 | 6/2005 | Koele et al. | |

* cited by examiner

MANUFACTURING INSPECTION OF FOLDED FEMININE HYGIENE PRODUCTS BY CASCADING EDGE AND SKEW DETECTION

CROSS REFERENCE TO RELATED APPLIATION

This application claims the benefit of U.S. Provisional Application No. 60/715,513, filed Sep. 9, 2005.

FIELD OF THE INVENTION

The present application relates to systems and processes for inspecting overlaid layers of material in a continuous manufacturing operation. More particularly, the present application relates to systems and processes for inspection of disposable absorbent articles in a continuous manufacturing process.

BACKGROUND OF THE INVENTION

There are many well-known varieties of feminine hygiene products configured for the absorption of human body fluids. Some of these absorbent articles, such as sanitary napkins and panty liners, have a pair of wings or flaps that extend laterally from the longitudinal side edges of an absorbent, central portion and are intended to be folded around the crotch area of the wearer's undergarment during use.

In the manufacturing process of these absorbent articles, a continuous web of layered materials typically is driven through a high-speed machine to form several hundred articles per minute. The web may be formed, for example, from a pair of thin, continuous layers (a backsheet and a topsheet) of a polymer film and/or non-woven web that retain a series of individual, pad cores that are spaced evenly apart along the longitudinal axis of the web. The process may include cutting each absorbent article from the continuous web of material, folding the pair of wings around the central portion, applying an adhesive to a release tape, and attaching the release tape to the wings (not necessarily in that order). The wearer removes this release tape to expose the adhesive that has transferred to the backsheet in order to attach the wings to the undergarment.

During the step of folding the pair of wings around the central portion, the article may be conveyed over one or more stationary, contoured rails, which are known in the art as folding plows or folding boards. The folding plows gradually fold each wing 180 degrees from the original plane of the conveyed, web material. Ideally, the wings are consistently folded along fold lines that are parallel to the longitudinal axis of the article so that the free ends of the folded wings come together approximately edge-to-edge. The free ends are aligned adjacent each other and desirably there is no gap or open space between the free ends.

Unfortunately, sometimes during the folding step, one or both of the wings of an article are folded into a skewed configuration, thereby resulting in a gap between the edges of the free ends of the wings. Generally, manufactured articles having this "skew" also may be excessively wrinkled or may have irregular folds. Similarly, one or both wings may fold-over on itself, either inwardly or outwardly. In either the skew or the fold-over situation, it is possible for some of the adhesive on the release tape to transfer to the topsheet that eventually comes into contact with the wearer's body, causing her considerable discomfort.

Accordingly, there is a need for an improved inspection system and process to inspect for wing-folding skew and fold-over of absorbent articles as they are manufactured, whereby any gap or over laid condition can be consistently detected.

Conventional methods for inspecting absorbent articles manufactured from a continuous web and detecting folding process variations in a cost-effective manner have been only partially successful. Many manufacturers use vision systems to produce an image from a composite article undergoing inspection and then analyze the image to detect the position of one or more components within the image. The position of the components are then compared to ideally desired positions to determine whether one or more components are properly positioned. Such an inspection system typically employs conventional video cameras for capturing visual and ultraviolet light that is reflected by and/or transmitted through components of the composite article in order to produce images of the components. After producing an image of the composite article, the image is analyzed to determine whether the components are properly positioned and registered with one another. Other inspection systems employ infrared detectors for producing infrared images of products ongoing formation by sensing infrared radiation emitted by heated components. These images are then compared with reference information to determine, for example, whether the product and components are properly positioned. Such systems are not well suited to inspecting products which have cooled, or which were never heated in the first instance. Still other systems attempt to identify overlapping engagement of panels which are irradiated with radiation. In such systems, an image is produced from radiation received from the irradiated panels. A position of the underlying edge is identified in the image and the underlying edge is compared with preexisting data to determine whether the underlying edge is present and/or properly positioned in the composite article. Such systems are not well suited for determining the presence and/or position of numerous components underlying other components or various components which are somewhat opaque to visible light. Additionally, these systems do not differentiate between gray scales.

Accordingly, there is a need for an improved vision system and method of inspecting and analyzing composite articles during manufacture, especially for identifying gap or skew or fold-over conditions between multiple components in an absorbent article through use of a cascading inspection system.

SUMMARY OF THE INVENTION

In one embodiment, a process for inspecting an article having overlying components is provided. The process comprises the following steps. An image is produced from an article. A first edge is identified within the image at a location where there is a substantially coarse contrast. A first discrete region is defined based on the location of the first edge. A location of a second edge is identified within the first discrete region at a location where there is a contrast. The location of the second edge is compared to a known parameter. A second discrete region is defined based on the location of the second edge. A location of a third edge is identified within the second discrete region at a location where there is a contrast. The location of the third edge is compared to a known parameter. The method includes the step of fitting the image to a defined gray scale for each discrete region. A center point is calculated for the article using the first edge and the second edge. A centerline of the article is determined. A skew of the article is calculated. A filter is utilized to enhance the contrast of the image in the discrete regions.

In another embodiment, the article comprises an absorbent article having a permeable topsheet and an impermeable backsheet having a core disposed between the topsheet and the backsheet. There is a pair of wings that extend laterally from longitudinal sides of the core. The wings have outer edges and are folded over the core such that the outer edges of the wings are adjacent each other. The alignment of the overlaying edges of the wings is determined and the alignment is compared to the skew of the article.

In yet another embodiment, a process is provided for inspecting an absorbent article constructed from multiple components including at least a permeable topsheet, an impermeable backsheet, and an absorbent core disposed between the topsheet and the backsheet. The process comprises the following steps. An image is produced from the absorbent article. The image of the absorbent article is filtered. In the image of the absorbent article, a nonlinear first edge is identified wherein the first edge is a location where there is a coarse change in contrast. In the image of the absorbent article, a second edge is identified wherein the second edge is a location where there is a coarse change in contrast. A center point of the absorbent article is calculated using the position of the first edge and the second edge. A centerline of the absorbent article is determined. A skew of the absorbent article is calculated. These known locations are utilized to define at least one region of the image for further analysis. A filter is utilized to enhance the contrast of the image in the defined region. In the defined region, a third edge is identified wherein the third edge is a location where there is a fine change in contrast. In the defined region, a fourth edge is identified wherein the fourth edge is a location where there in is a fine change in contrast. The skew of the third edge and the fourth edge within the defined region is calculated. The skew of the third edge and the fourth edge is compared to known parameters for the absorbent article.

Other aspects, variations, and embodiments of the improved inspection system and method of inspecting and analyzing the operation of a folding system will become apparent from the following description, the accompanying drawings, and the appended claims.

DETAILED DESCRIPTION OF THE INVENTION

An improved inspection system and process is provided for the high speed inspection of folded, absorbent articles such as sanitary napkins and panty liners. As will be described, the inspection system includes numerous improvements that, in combination, detect any unacceptable gaps and undesirable wrinkling and skewing of the pads, particularly the wings when folded during operation. The improved inspection system and process also detects the occurrence of fold-over (in both the inward and outward directions) of wings or flaps of such absorbent articles produced using a folding system. The inspection system and process of the present invention is useful in the production and inspection of absorbent articles of the type described in U.S. Pat. No. 6,391,011 issued May 21, 2002 to Davis et al., which patent is incorporated herein by reference.

Overview of the Folding System

It should be understood that the folding system described herein refers to the folding of discrete, absorbent articles that have been formed and cut from a continuous moving web, and that such absorbent articles may also include adult and baby diapers, facial tissues, and other implements having folds.

Figure 1:
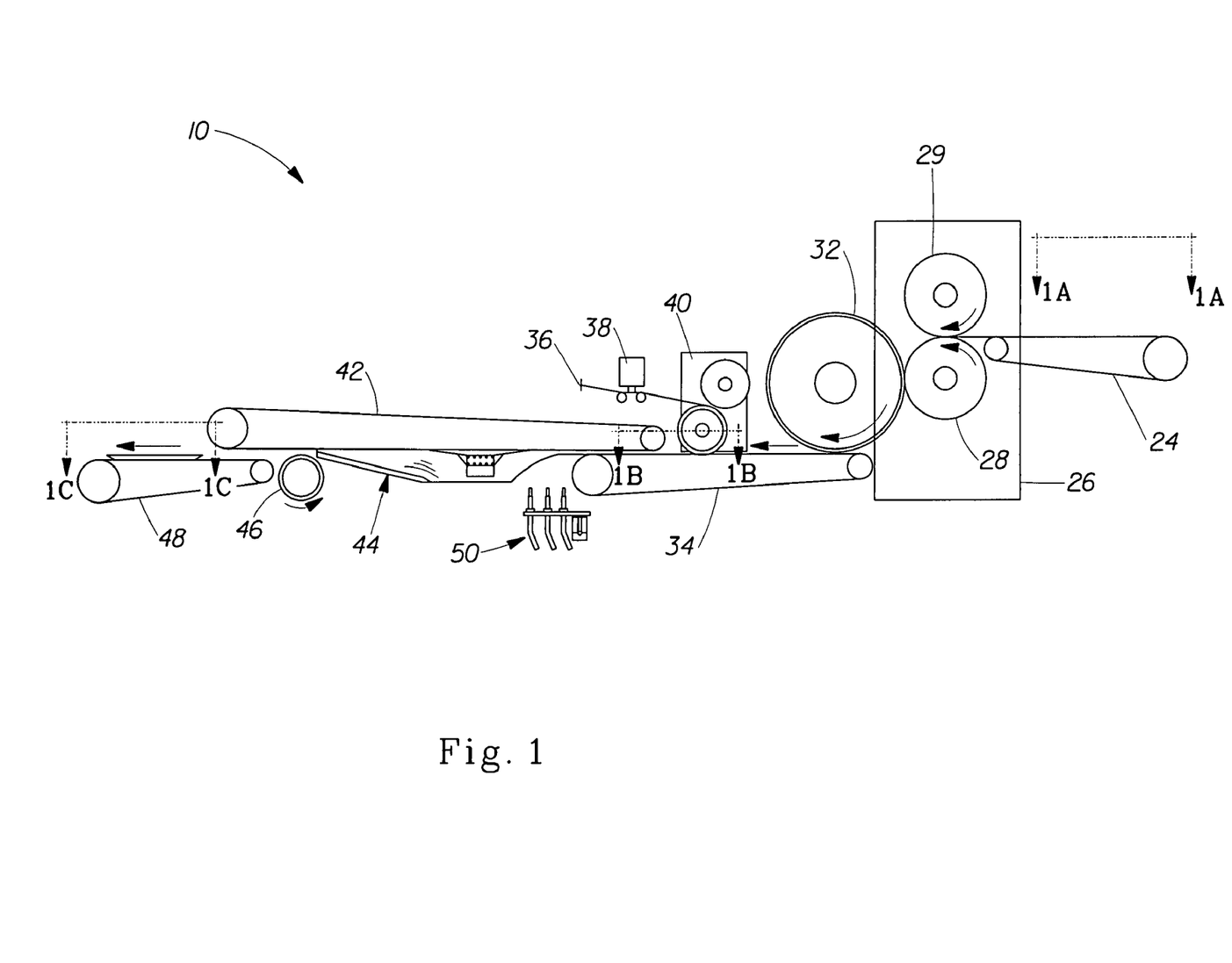
FIG. 1 is a schematic illustration of a folding system that may be used in a folding process.
Figure 1A:
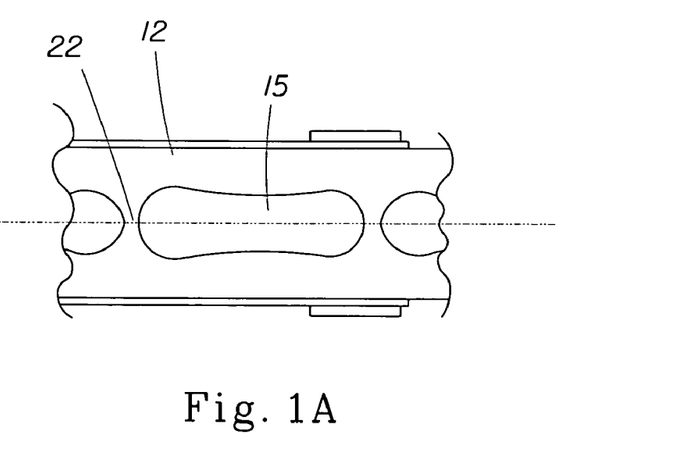
Figure 1B:
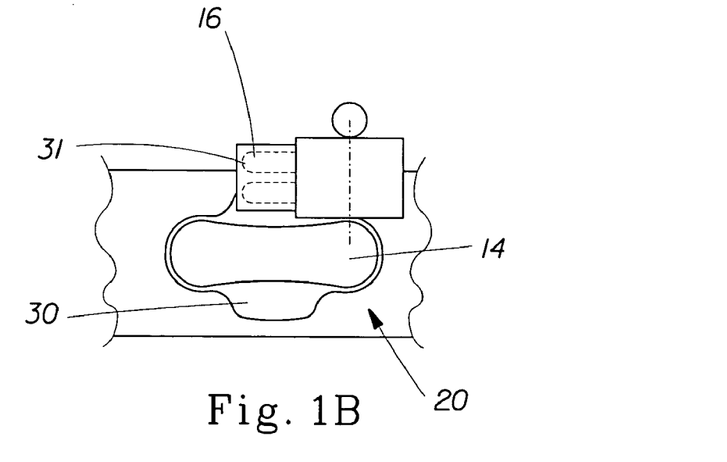
Figure 1C:
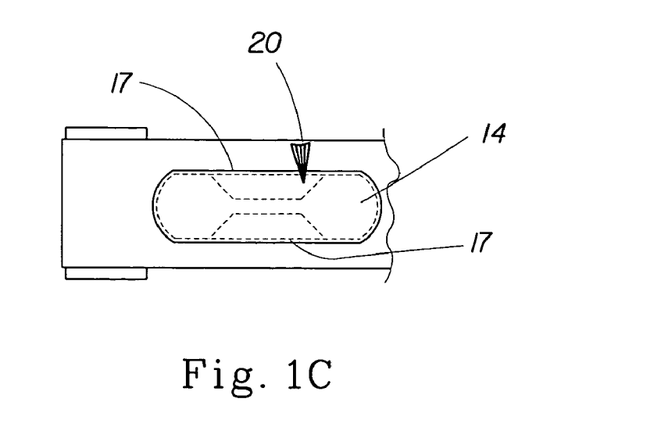

FIG. 1 is a schematic illustration of a folding system, generally designated 10, that conveys a continuous web 12, cuts each absorbent article 20 (also referred to as a pad 20) from web 12 at a rate of several hundred pads per minute, applies a release tape 16 having an adhesive to each pad 20, and folds each pad 20 into a folded configuration for further processing and/or packaging. Web 12 may include a perforated film or non-woven web topsheet and a liquid impervious backsheet, each of which may be formed from a thin polymer film or non-woven webs as is well-known in the art of making disposable absorbent products. Web 12 may be approximately 200 millimeters wide and fed off a roll (not shown) to folding system 10. A continuous series of elongated, pad cores 15 (view A-A) are aligned end-to-end along a longitudinal web axis 22 of web 12 and spaced evenly apart. Each pad core 15 may be any of known materials and configurations for pad cores in sanitary napkins, panty liners and other absorbent articles. Such absorbent materials include paper, cotton and/or other suitable synthetic or natural products. Each pad core 15 is retained between the top and backsheets, as is well-known in the art, to form a central chassis 14 (view C-C) having a pair of longitudinal side edges 17.

Folding system 10, like many industrial conveyor systems, has a drive side and an operator side. In FIG. 1, folding system 10 is viewed from the operator side, and the flow of web 12 is from right to left. Web 12 is conveyed along a first vacuum conveyor 24 (also referred to as an input conveyor) that is perforated and in fluid communication with a vacuum source (not shown) such that the topsheet of web 12 is held against conveyor 24, as is well-known in the art. Web 12 next is conveyed through a cutting assembly 26 having a rotary knife 28 that cuts the individual absorbent articles 20 from web 12. (For description purposes, an individual pad shall often be referred to herein, although it should be kept in mind that during steady-state production, tens of pads are formed each second.) A first wing 30 and a second wing 31 are formed on opposite sides of central chassis 14. Pad 20 is next transferred by a transfer roll 32 to the top of a second vacuum conveyor 34 (also referred to as a transfer conveyor). Above second vacuum conveyor 34, an adhesive applicator 38 intermittently applies an adhesive to a continuous tape 36, which then passes through a phase-driven, cut-and-slip knife 40 to form a continuous series of individual release tapes 16 with adhesive. One end of each release tape 16 is then bonded to the backsheet of second wing 31 of each pad 20, allowing the free end of release tape 16 to extend laterally beyond wing 31. Pad 20 is next conveyed from the top of second vacuum conveyor 34 to the bottom of a third vacuum conveyor 42 (also referred to as a wing-folding conveyor).

Pad 20 is conveyed by third vacuum conveyor 42 so that wings 30, 31 slide against a pair of folding plows 44, also referred to as folding rails or folding boards, in order to fold each of wings 30, 31 around central chassis 14 to form the folded pad configuration shown in view C-C. The configurations of folding plows 44 are particularly important relevant to folding wings 30, 31 on pad 20. As pad 20 is conveyed along folding plows 44, a plurality of blowers 50 positioned beneath plows 44 provide a positive air pressure profile to help hold wings 30, 31 against plows 44. Pad 20 is next conveyed through a bonding roll 46 to press release tape 16 against wings 30, 31 so that the adhesive on release tape 16 bonds completely to wings 30, 31. Pad 20 next is conveyed from the bottom of third vacuum conveyor 42 to the top of a fourth vacuum conveyor 48 (also referred to as an output conveyor), from where pad 20 is conveyed to a subsequent inspection processes as will be described herein.

Figure 2:
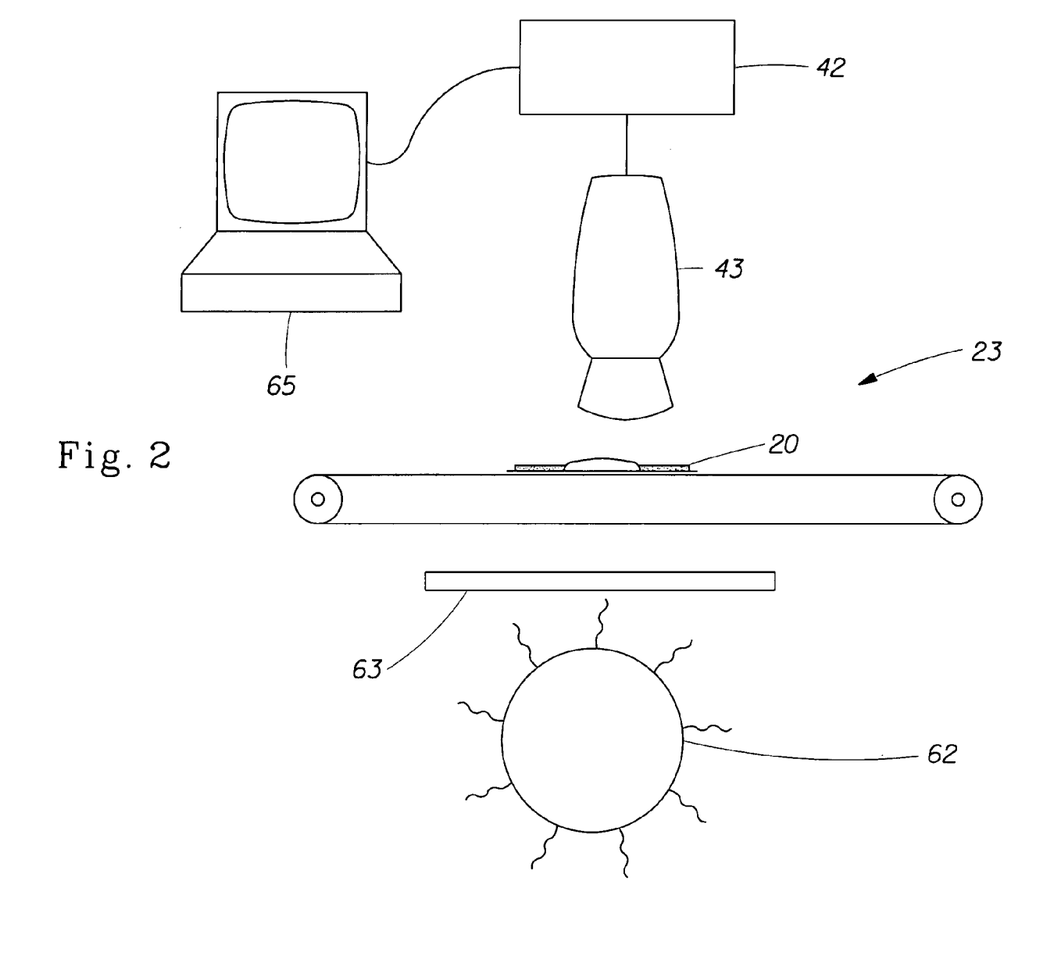
FIG. 2 is a schematic illustration of an inspection system in accordance with the present invention.

Next, as illustrated in FIG. 2, pad 20 is conveyed through an inspection operation which includes capturing an image of pad 20 and analyzing the image. Pad 20 passes through an inspection station where a light source 62 is positioned opposite a camera 43 so the light passes through various components of pad 20 and is captured in an image produced by camera 43. In one embodiment of the present invention, backlighting light source 62 is disposed on the opposite side on the pad 20 from camera 43. Alternatively, a diffuser 63 can provide for proper diffusion of light from the backlighting light source 62 such that a substantially constant intensity of light is created across the area of the pad 20 being inspected. In this embodiment, those components of the absorbent article which are opaque or are substantially opaque, will produce dark zones in the electronic image produced by camera 43. Those areas of the pad 20 which are relatively translucent will appear as light zones. Backlighting light source 62 are preferably strobed at a rate directly proportional to the rate at which the pad 20 travels along the machine direction of the fabrication system whereby the absorbent articles contained in the pad 20 are effectively "stopped" for inspection. While a single light source 62 is illustrated, multiple light sources 62 may be utilized for proper light transmission through pad 20. Where camera 43 is a high shutter speed camera, the shutter speed can be synchronous to the strobe such that the shutter is open upon each strobe of light source 62.

This image is then analyzed using an image analyzer 42. Image analyzer 42 is operatively connected to camera 43 and receives the image transmitted from camera 43 to identify the position or location of components within the image. Relative positioning of components in pad 20 such as the location of the free ends of wings 30, 31 can be established using the inspection system. While inspection station is described as being located immediately after pad 20 passes through bonding roll 46, such an inspection could occur at various other locations and numerous times throughout the manufacturing process for absorbent article 20.

Figure 3:
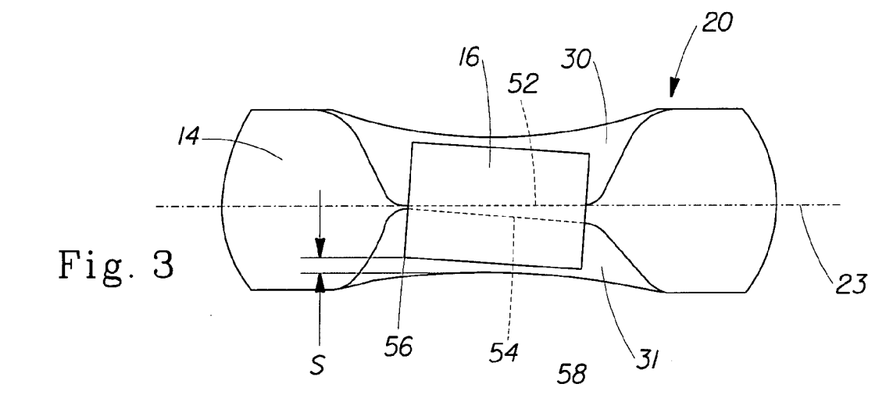
FIG. 3 is a top view of a folded pad having a wing-fold skew.
Figure 4:
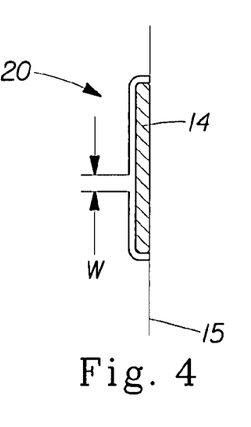
FIG. 4 is an end view of the pad shown in FIG. 3.
Figure 5:
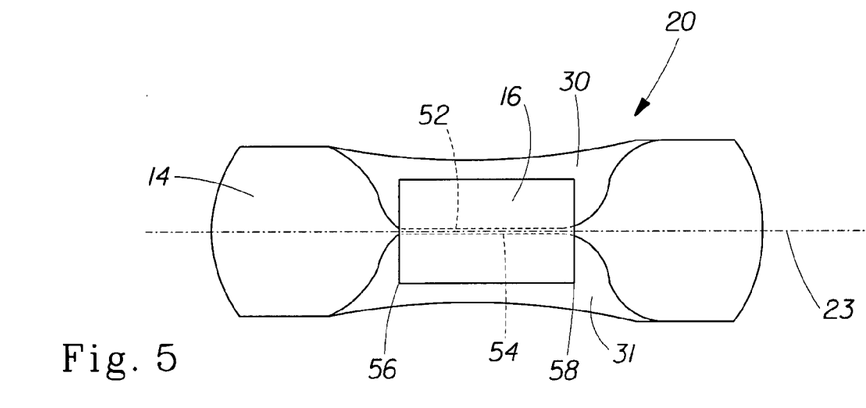
FIG. 5 is a top view of a properly folded pad.
Figure 6:
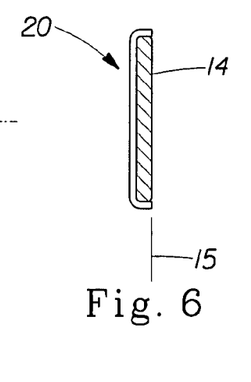
FIG. 6 is an end view of the pad shown in FIG. 5.

FIG. 3 is a top view and FIG. 4 is an end view, showing a pad plane 15, of an improperly folded pad 20. FIG. 5 is a top view and FIG. 6 is an end view of a properly folded pad 20. In FIG. 5, second wing 30 is shown to have an edge 52 approximately aligned along longitudinal web axis 22 and first wing 31 is shown to have an edge 54 that is also aligned with longitudinal web axis 22 and touching or nearly touching edge 52 at a longitudinal pad axis 23. A slight overlap of edges 52, 54 may also be considered to be acceptable. However, for the improperly folded pad 20 shown in FIG. 3, edge 54 of first wing 31 is angled with respect to longitudinal pad axis 23, thereby resulting in a wing gap "W" and a skew "S". One side of release tape 16 has a first corner 56 that is closer to longitudinal pad axis 23 than a second corner 58. Skew shall be defined herein as the difference in distance from longitudinal pad axis 23 of first corner 56 and second corner 58. Skew has been observed for some folding processes to be in the range of about 1 to 6 millimeters. As noted earlier, when pad 20 is improperly folded with a skew greater than about 2 millimeters, it is possible for some adhesive on release tape 16 to transfer to the topsheet of pad 20, thereby possibly resulting in the undesirable situation of adhesive sticking to the body of the wearer. Skew may also be accompanied by undesirable wrinkling of pad 20. It is also apparent that gap "W" is an undesired condition between edges 52, 54 with or without skew "S".

Folding Plows

Figure 7:
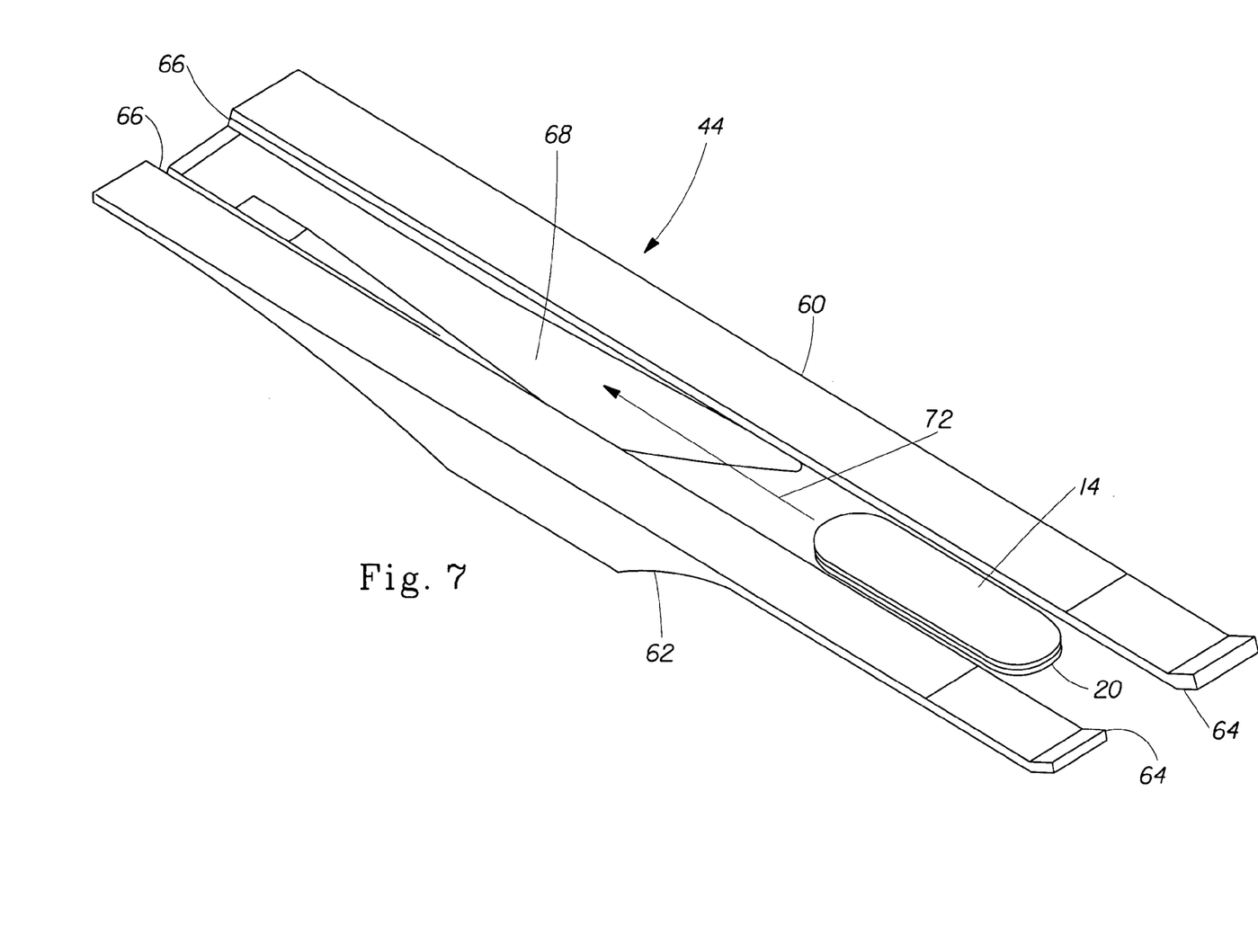
FIG. 7 is an isometric, top view of a pair of folding plows of the folding system shown in FIG. 1.
Figure 8:
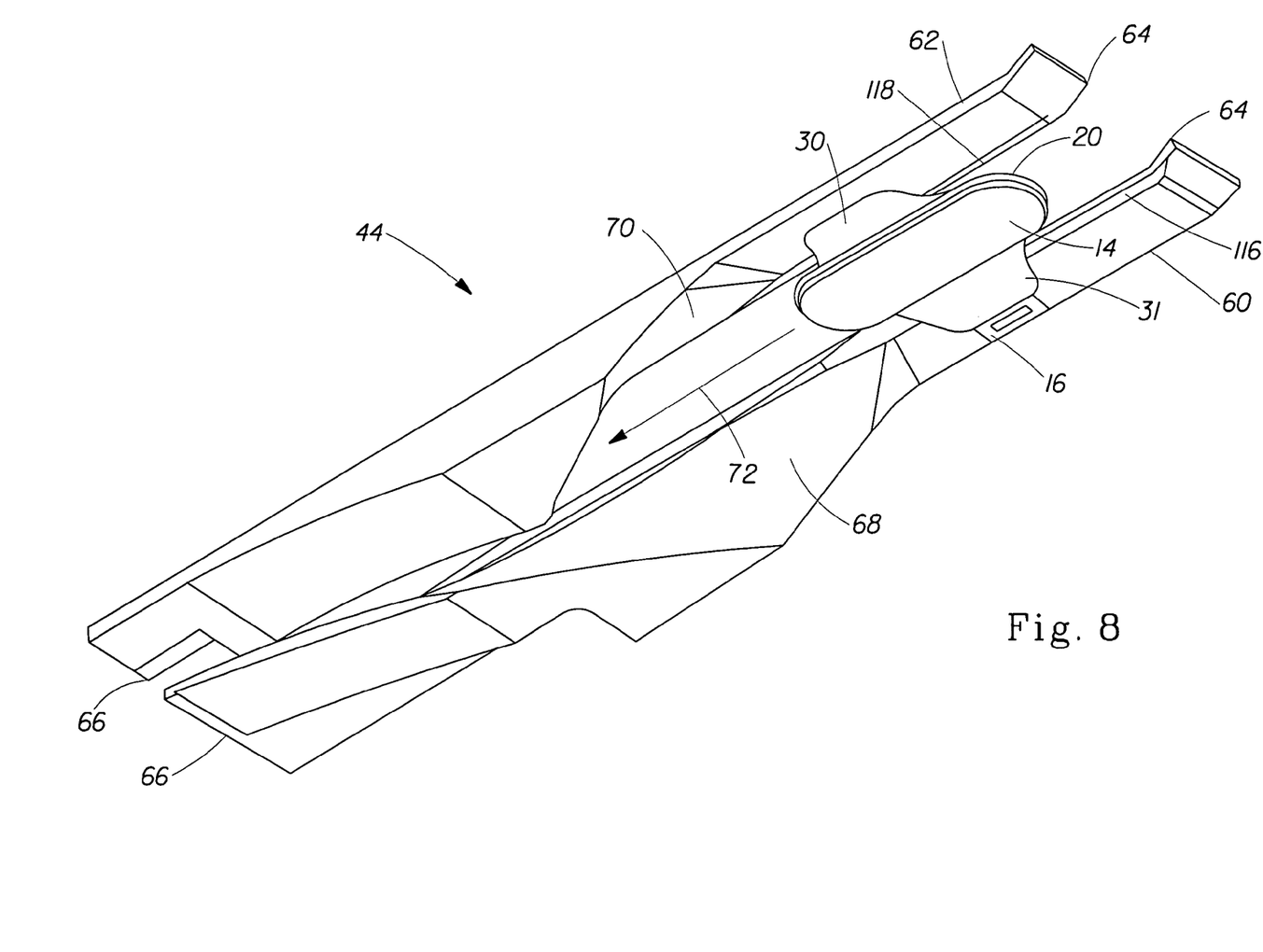
FIG. 8 is an isometric, bottom view of the pair of folding plows shown in FIG. 7.

FIG. 7 is a top isometric view and FIG. 8 is a bottom isometric view of folding plows 44, which include a drive side plow 60 and an operator side plow 62. Pad 20 is conveyed along folding plows 44 by third vacuum conveyor 42 (FIG. 1) in the direction indicated by arrow 72. Each of folding plows 44 may be formed from a metal or other hard, rigid, wear-resistant material that may be formed with a smooth surface. Folding plows 44 may also be coated with a lubricious and/or wear resistant material to reduce friction at the interfaces with pad 20. The length of folding plows 44 may vary significantly, but may be approximately in the range of 25 to 100 centimeters. Drive side plow 60 and operator side plow 62 are mounted beneath third conveyor 42 and are parallel and spaced apart to define a plow entrance 64 and a plow exit 66. Drive side plow 60 has a contoured surface 68 that contacts the backsheet side of wing 31 and release tape 16 of pad 20, as shown in FIG. 8. Operator side plow 62 has a contoured surface 70 that contacts the backsheet side of wing 30 of pad 20. As is well-known in the art, contoured surface 70 is shaped to fold wing 30 around central chassis 14 before contoured surface 68 completes the folding of wing 31 around central chassis 14 so that release tape 16 may be bonded to the backsheet side of folding wing 30 at the end of the folding process.

In this bottom view of folding plows 44, showing first wing 31 and release tape 16 sliding against contoured surface 68 of drive side plow 60, and second wing 30 sliding against contoured surface 70 of operator side plow 62. The additional mass of release tape 16 extending from wing 31 contributes to the frictional, aerodynamic and inertial loading effects acting on wing 31. It is not uncommon for wing 31 to skew during the folding process more often than wing 30.

Rotary Knife

Another contributor to wrinkling during the pad manufacturing process is uneven "cross-web tensioning" that may occur during the cutting of individual pads from the moving web. As shown in FIG. 1, web 12 passes between a rotary knife 28 and a compression roller 29 so that individual pads are cut from web 12. As described earlier, the web 12 is formed form a plurality of relatively thick, pad cores 15 retained between thin top and backsheets, so that the wings 30, 31 of each pad 20 are much thinner than central chassis 14. Because of this thickness variation, the tension of the web material in the longitudinal direction may vary across the width of web 12 as it passes between compression roller 29 and rotary knife 28. This tension variation may lead to wrinkling of pad 20 as it is cut from the web 12, and the wrinkling may eventually contribute to wing-fold skew and/or fold-over.

Bonding Roll

Referring yet again to FIG. 1, pad 20 exits from folding plows 44 and engages bonding roll 46 as described earlier. Skewing and fold-over has also been determined to occur during this step of the pad manufacturing process. Bonding roll 46 positioned near the exit end of folding plows 44 and beneath third vacuum conveyor 42. A pad (not shown) exits folding plows 44 and engages bonding roll 46. As described earlier, release tape 16 may initially be adhered to wing 31 of pad 20 and then folded around central chassis 14 by drive side plow 60. Prior to passage through bonding roll 46, release tape 16 may not yet be completely bonded to wing 30 on the operator side. Therefore, wing 31 with the extra mass of release tape 16 is highly susceptible to skewing when wing 31 and tape 16 impact bonding roll 46.

Method for Inspecting the Absorbent Article

Following the application of release tape 16 and passing through bonding roll 46, the fully assembled pad 20 passes through inspection station 23. As shown in FIG. 2, inspection station 23 and comprises a camera 43 and light source 62 and image analyzer 42 and display device 65. The inspection station 23 can also include a diffuser 63 to diffuse the light emitted by light source 62. Light emitted from light source 62 passing through pad 20 is detected by camera 43. Camera 43 can be any suitable type of camera 43 which is capable of creating at least a two-dimensional image of a single absorbent article located beneath it at the inspection station 23. For example, camera 43 can be a high shutter speed camera 43 having a matrix of photodiodes disposed therein whereby the matrix of photodiodes electronically produces a still picture image of the absorbent article in the inspection station 23. In the inspection station 23, camera 43 is mounted on the opposite side of the absorbent article 20 from the light source 62, so that the camera 43 produces an image from the light passing through the various components of the absorbent article.

A suitable inspection system 48 for use in the present invention, including camera 43, video image display device 65, and image analyzer 42, is available from Cognex Corporation, Natick, Mass.; USA, as CHECKPOINT 800 or CHECKPOINT 900 or IN-SIGHT EXPLORER. Suitable software for collecting displaying, and analyzing the visual images so collected, of individual ones of the absorbent articles being fabricated in the manufacturing operation, is also available from Cognex Corporation and, for example, such software can be in a visual basic programming format. The image analyzer 42 can utilize a user interface in a spreadsheet format or a user interface having a combination spreadsheet format with some MICROSOFT WINDOWS drop down menus or the user interface can simply be a user friendly MICROSOFT WINDOWS format.

The above described inspection system 48 has a rate capacity of producing a visual image of each and every pad 20 produced by the manufacturing process. Indeed, it is desirable to the line operator that the inspection system does produce a visual image of each and every work piece at a "high speed." As used herein, "high speed" indicates a capability of producing at least about 200, and in one embodiment at least 400 or 500, yet in another embodiment at least about 1500 visual images per minute from the camera 43 of the nature described herein for use in the invention. The number of images collected per minute is controlled by signals, from the processing line, indicating the frequency of passage along the processing line, of pads 20. These images can then be analyzed as described herein and stored in a memory storage device.

The image produced by camera 43 provides an electronic or digital representation of the positional relationships of the intensity of light either absorbed or passing through various components of the absorbent article, permitting an inspection of the presence and relative placement of the various components. This electronic image is transmitted to image analyzer 42 and the image can be displayed to a user on display device 65. While it is possible to analyze the entire image, it is preferable to analyze only selected areas or regions of the image. Thus, with regard to FIG. 9, discrete regions in the image can be analyzed independently. For example, the discrete region or area 47 can be analyzed to determine the position of the leading edge of the absorbent article; area 48 can be analyzed to determine the position of the trailing edge of absorbent article; area 51 can be analyzed to determine the position of the score line with respect to the leading edge; area 52 can be analyzed to determine the position of the score line with respect to trailing edge; area 53 can be analyzed to determine the position of the free end of the wing 30; and area 54 can be analyzed to determine the position of the free end of the wing 31. These analyses can be accomplished by determining the exact location within the particular area or discrete region of the image where there is a change in contrast or light intensity. For example, a change in contrast occurs at the location where the image changes from dark to light or from light to dark. Each change in contrast or light intensity indicates the location of an edge of a component. Additionally, these areas can be analyzed to determine the extent or uniformity of various components or edges by conducting an analysis of the grayness within one particular area or the grayness between various areas.

In particular, the image analyzer 42 can determine grayness by assigning a gray scale to each image or region within an image or a portion thereof to be analyzed. An image may have black areas and white areas which represent a coarse change in contrast from each other. The black areas within the image are opaque locations where the light emitted from light source 62 is unable to penetrate or pass through pad 20 in order to be captured in the image by camera 43. The white areas are translucent or are places where the light easily penetrates or is transmitted through pad 20 and is captured in the image by camera 43. This same image may also have various shades or levels of gray or grayness where light is partially transmitted through various components of pad 20 and where portions of the light is partially blocked by the components. In analyzing the image, image analyzer 42 can assign a scale having values from between 1 and 20 to the black and white areas. For example, a value of 1 can represent black or no light passing through pad 20 and a value of 20 can represent white or substantially all the transmitted light passing through pad 20. Relative values between 1 and 20 are then assigned to corresponding levels of grayness between the black in the image and the white in the image. These gray scale values are relative and are based on the shades of black, white and gray in the particular image or portion of the image being analyzed. Thus, a gray scale from 1 to 20 is used to calibrate or refine the image or portion of the image in order to improve the ability to determine the contrast between shades of gray defining the edges of various components within pad 20. In any such portion of the image, the darkest gray will be assigned a value of 1 and the lightest gray will be assigned a value of 20. This allows refinement of the contrast between gray scale levels in each image or portion of the image analyzed in order to provide for improved identification of components and edges by using a fine change in contrast for slight changes in the shades of gray representing only small variations in the amount of light passing through adjacent components within the image.

Image analyzer 42 can utilize filters applied to each discrete region in order to adjust or refine the gray scale within portions of the image. Image analyzer 42 may be provided with various types of filters known in the art including optical filters, electronic filters, and any combinations thereof. One or more of such filters are useful in removing ambient, reflected and scattered light to improve the quality of the image being analyzed.

As each change in contrast represents the location of an edge, image analyzer 42 can help determine whether each component or each edge thereof in the image of the absorbent article is in its desired position when compared with the manufacturing tolerance data for that component or edge. The image analyzer 42 may further be configured to compare identified positions with other existing reference data (e.g., ideal, previous or predetermined fixed and/or relative position data, as applicable) to thereby determine whether one or more components are properly present and positioned in the pad 20. If the position of a component is outside of a predetermined tolerance range, the inspection system can provide a signal to the controller for the folding system signaling the need for a system adjustment and, if necessary, a signal to reject or discard the defective absorbent article. An alarm (such as an audible alarm or a visible alarm, such as one provided on a display device 65) may also be provided upon determining that one or more components of a pad 20, or a series of pads 20, are mispositioned, and a display of the image or portion thereof can be displayed on display device 65 to an operator for monitoring, tracking or diagnostic purposes.

The image analyzer 42 can be configured to determine the positions of variations in the image produced by the camera 43, and thus the edge positions of components in the pad 20, either as fixed positions or relative positions, or a combination of both. Thus, the image analyzer 42 may determine the edge position of a pad 20 component relative to a fixed point, edge or discrete region of or in the image, relative to another component or the edge of another component in the image, relative to a registration mark on or about a component of the pad 20, etc. As one example, the image analyzer 42 may first determine the edge position of a first component as a fixed position in terms of x and y coordinates representing the machine and cross directions respectively, and then determine the edge position of a second component (or another edge position of the first component) relative to the previously determined edge position of the first component.

Figure 10:
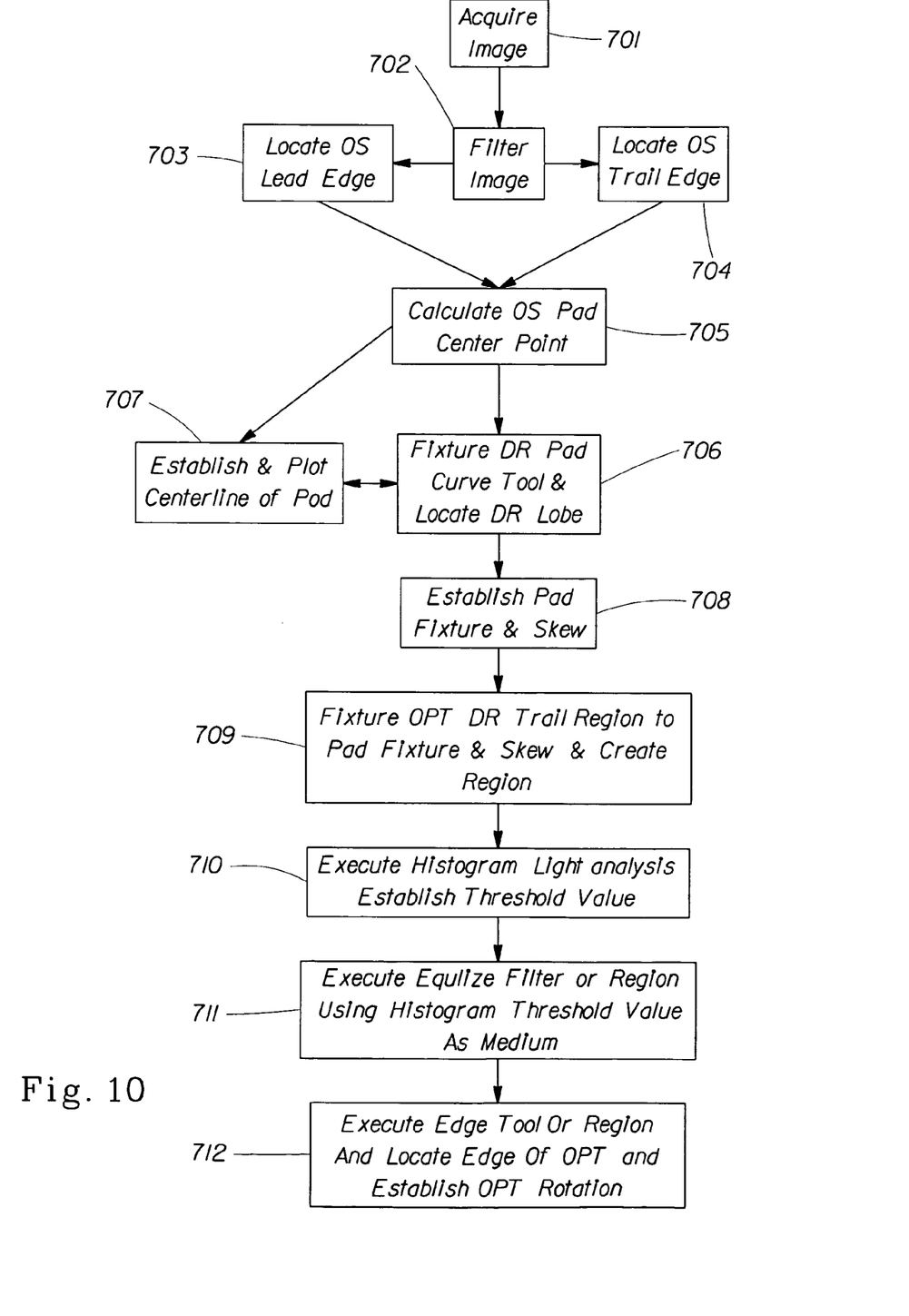
FIG. 10 is a flow chart describing a method for inspecting a folded pad.

FIG. 10 is a flowchart illustrating the steps in the cascading inspection system and process to inspect pads 20 for a skew or gap. The inspection process begins with the acquisition of an image from pad 20 using camera 43 [701]. The image is transmitted to image analyzer 42 wherein the image is analyzed to determine the locations of various components and edges within the image. Filtering of the image to enhance the sharpness of the image can performed at this and/or various other stages during the inspection process [702]. Initially, at least one edge is located within the image where a coarse change in contrast exists where the light intensity changes from substantially white to substantially black or vice versa [703]. This coarse contrast represents a first edge which may correspond to the operator side leading edge of pad 20. The characteristics of the first edge can also be determined, for example, the characteristics of the edge may indicate that the edge is linear or nonlinear such as a semicircular arc or other curved line. Next, the edge on the opposite end (e.g., operator side trailing edge if leading edge was located first or vice versa) can be located in a similar manner as described [704]. Additionally, a reference or datum can be calculated from the location and characteristics of either one of the leading edge or trailing edge [705]. Such a datum can be the operator side center point of pad 20. Using the first edge and a center point, the center line of pad 20 is established and calculations prepared to establish the drive side components [706]. A plot of the center line can be incorporated into the image [707] and the angular alignment of pad 20 can be calculated from which to determine any skew of wings 30, 31 [708].

Figure 9:
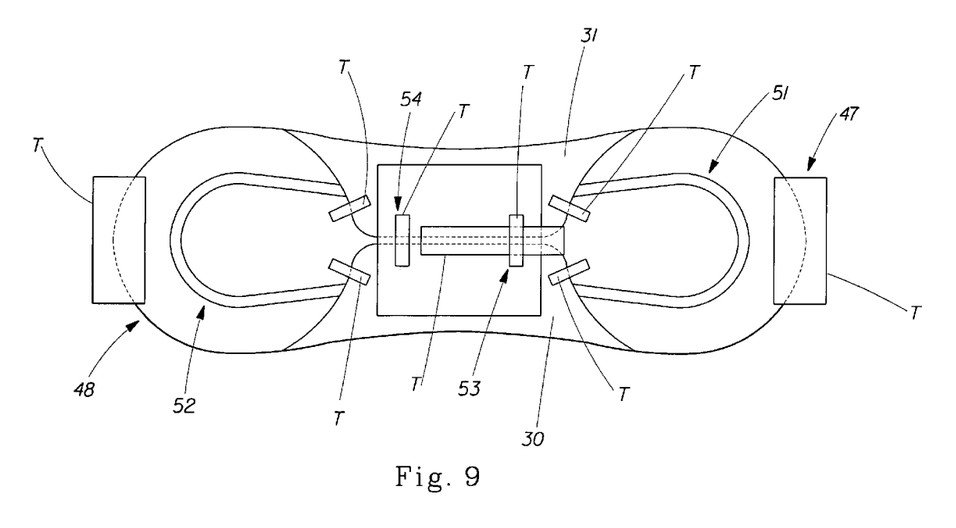
FIG. 9 is a top view of an illustrative image of a folded pad having tools located thereon.

Discrete regions are defined in which each edge is expected to be detected. Such discrete regions define locations for the placement of windows. These windows are sometimes referred to as "tools". FIG. 9 illustrates the tools T of one embodiment according to the invention. Each tool T can be a rectangular area within which the image system scans for changes in light contrast indicating a component such as an edge. In general, the inspection system looks at the pixels within the rectangular area from one end to the other. The image analyzer 42 is programmed to look for changes in gray scale such as changes or transitions from lighter to darker shades or vice versa to identify the existence of an edge. If the image analyzer 42 can not find a particular edge, the tool may be redefined in a variety of ways. For example, the tool may be repositioned, changed in size, rotated or otherwise modified either manually or automatically, whether based on known tolerances or expected variations or other conditions.

Next, referring back to FIG. 10, a discrete region can be identified and a tool placed in an appropriate location to identify the next component within the image. The placement of this tool can be based on predetermined historical data relative to the location of the previously identified component [709]. An edge within this discrete region can then be identified. For example, this tool can be placed in a location to identify the position of the edge representing a free end of wing 30. In a similar manner using the tool, various components within the range of this discrete region can be located by determining the locations where there are changes in contrast or gray scale [710]. An analysis of the discrete region is performed and the gray scale is refined and calibrated if needed utilizing any appropriate filtering mechanisms while forcing the shades of gray to fit within the applied gray scale [711]. Substantially finer changes in contrast or light intensity are identified defining edges of the various components within the discrete region. In this manner, edges can be defined representing the release tape 16 and any skew associated with the free end of wing 30 [712].

Next another discrete region can be identified and a tool placed in an appropriate location to identify the next component within the image. The placement of this tool is based on predetermined historical data relative to the location of at least one of the previously identified components or edges. An edge within this new discrete region can then be identified. For example, this tool can be placed in a location to identify the position of the edges representing the free end of wing 31 and release tape 16. In a similar manner using the tool, various other components within the range of this discrete region can be located by determining the locations where there are changes in contrast or gray scale. An analysis of the discrete region is performed and the gray scale is refined and calibrated if needed utilizing any appropriate filtering mechanisms while forcing the shades of gray to fit within the applied gray scale. Substantially finer changes in contrast or light intensity are identified defining edges of the various components within the discrete region. In this same manner the angular orientation of pad 20 is known as well as the angular alignment of edges representing wing 30, wing 31 and their corresponding free ends. From this data the skew and any gap associated with pad 20 can be determined. Consequently, this inspection system provides for the comparison between the actual positions of the components and edges in pad 20 with their desired positions in order to determine whether the pad 20 is acceptable.

If desired, yet another discrete region can be identified and a tool placed in an appropriate location to identify yet another component within the image based on the locations of the previously identified components or edges. In the same manner described, an edge within this new discrete region can then be identified and so forth. Similarly, an analysis of the discrete region can be performed by refining the gray scale for an even finer change in contrast. In this manner, the inspection system defined herein provides a way to cascade from one defined component to another with the ability to refine the gray scale for detection of very fine changes in contrast.

In particular, the inspection system described herein identifies each subsequently defined discrete region based on a previously located component and the inspection system also scans for changes in contrast or light intensity within the tools. As noted above, changes in light intensity indicate the location of an edge. Each tool scans its corresponding discrete region to identify any changes in light intensity of the image and thereby determine the location of the edge. In the event that the edge is not located within the defined tool during the scanning of the defined tool, the tool is calibrated. This calibration or refinement may include assigning a gray scale value to the darkest and the lightest portions within the tool with incremental contrast changes being assigned corresponding gray scale values as previously described. The shades of gray within each tool are forced to fit a normal distribution thereby enabling the inspection system to identify relatively fine changes in contrast. In this manner, most any change in intensity or contrast can be detected. Thereafter, the determined presence and/or position of the component (e.g., an edge) is compared with predetermined data to determine whether the edge is properly positioned in pad 20. Next another tool is established at a known or predetermined position relative to the previously identified edge. The location of this tool is based on data or information programmed into the inspection system. Thus, the desired position (distance, orientation, etc.) of a second tool is known based on the location, expected manufacturing tolerances, and other characteristics of the previously identified edge. Once an edge is defined within the second tool, a third tool can be established at a known or predetermined location relative to the edge identified in the second tool. Once an edge is defined within the third tool, a fourth tool can be established at a known or predetermined location relative to the edge identified in the third tool, and so on.

For pads 20 of a particular configuration, once a center line and a known point is established, discrete regions or tools in which components of pad 20 are expected can be identified. The image analyzer 42 can then search the image for other components. For example, free end of wing 31 should fall within a predefined distance in the machine direction relative to the leading edge of pad 20 and within a predefined distance in the cross direction relative to the center line of pad 20. From these parameters a predetermined tool or discrete region can be identified in which to locate the edge which corresponds to the free end of wing 31. In a like manner, once the edge defined by the free end of wing 31 is identified, a tool or discrete region can be identified in which to find another component based on the location of the edge defined by free end of wing 31 as well as any of the previously defined components. Discrete regions or tools can cascade from one or more identified edges and components to the next. In this manner, components can be identified within expected tolerances using tools that cascade from one edge to the next edge. Thus, multiple overlaid components within an article can be identified and their locations compared against existing data in order to determine whether the components are in the proper locations. Thus, this cascading inspection system provides for the identification of component locations based on their relative positions relating to various other components within the absorbent article.

While the free ends of wings 30, 31 are described as the primary components of consideration, it should be understood that, as used herein, the term "component" shall include not only discrete objects such as wings 30, 31, elastic bands, free ends, release tape 16, but also objects yet to be formed into discrete objects (e.g., objects yet to be severed into discrete objects from a continuous sheet or pad 20 of material), particles (e.g., super gelling material or polymers), adhesives, lotions, ointments, and other substances, as well as portions or characteristics of any such components including, for example, fold lines, bond lines (e.g., ultrasonic bond lines), bonded or adhered regions, edges and registration marks applied to or about components for subsequent detection during a manufacturing or inspection process. Indeed, the teachings of the invention can be used to detect the presence and/or position including physical, optical, and component structural properties for any absorbent article or pad 20 under observation.

In an alternative embodiment, light source 62 is an ultraviolet light source that is disposed on the same side of the absorbent article as camera 43. In this version, optical brighteners are incorporated into various components of pad 20 such that the optical brighteners are activated by the ultraviolet light to produce light in the visible wavelength. Housing 42 prevents camera 43 from seeing visible light other than that emanating from pad 20. In this way, camera 43 creates an image of only those components of the pad 20 which include optical brighteners. Those components of pad 20 which do not contain optical brighteners do not react to the ultraviolet light to produce light at a visible wavelength and therefore will not appear in the image produced by camera 43. In a somewhat similar manner, an infrared image can be produced and analyzed using the inspection system of the present invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

Although a cascading inspection system and method of inspecting the operation of a folding system has been shown and described with respect to certain aspects, variations, and embodiments of absorbent articles, such as sanitary napkins and panty liners, various other articles and processes can be utilized, including, for example, flexible bags, baby and adult diapers, facial tissues, wipes, medical garments, clothing, and other implements. Moreover, it should be understood that various modifications and uses within the scope of the following claims may occur to those skilled in the art.

What is claimed is:

1. A method of inspecting an absorbent article using a camera and an image analyzer, wherein the absorbent article is constructed from a plurality of layered components including at least one permeable topsheet, an impermeable backsheet, with a pad core disposed between the topsheet and the backsheet, the method comprising the steps of:
    producing an image from the absorbent article;
    identifying at least one edge in the image, the edge comprising a location in the image where there is a contrast;
    defining a first discrete region in the image based on the location of the at least one edge;
    identifying at least one edge within the first discrete region, the edge comprising a location in the first discrete region where there is a contrast;
    Calculating a center point of the image using the previously identified edges;
    Determining a centerline of the image;
    Calculating a skew of the image from the centerline;
    defining at least one other discrete region in the image;
    identifying at least one other edge within the at least one other discrete region in the image;
    comparing the at least one other edge to the skew of the image.

2. The method according to claim 1, further comprising the step of utilizing at least one filter to enhance the contrast of the image in at least one of the defined regions.

3. The method according to claim 1, wherein the first edge further comprises, a nonlinear first edge.

4. The method according to claim 1, wherein, in the step of identifying at least one other edge within at least one other discrete region in the image, the at least one other edge comprising a location in the at least one discrete region where there is a fine contrast.

5. The method according to claim 1, further comprising the step of calculating a skew of the at least one other edge within the at least one other discrete region.

6. The method according to claim 5, further comprising the step of comparing the skew of the at least one other edge to a known parameter for the particular article.

7. The method according to claim 1, further comprising the step of applying a filter prior to the step of identifying at least one edge in the image.

8. The method according to claim 1, wherein each discrete region is located relative to at least one edge using a predetermined parameter based on the type of article.

9. A process for inspecting an article having overlying components using a camera and an image analyzer, the process comprising:
    producing an image from the article;
    identifying a first edge within the image at a location where there is a coarse contrast;
    defining a first discrete region based on the location of the first edge;
    identifying a location of a second edge within the first discrete region at a location where there is a contrast;
    comparing the location of the second edge to a known parameter;
    defining a second discrete region based on the location of the second edge;
    identifying a location of a third edge within the second discrete region at a location where there is a contrast;
    comparing the location of the third edge to a known parameter;
    fitting the image to a defined gray scale for each discrete region;
    calculating a center point of the article using the first edge and the second edge;
    determining a centerline of the article; and
    calculating a skew of the article.

10. The method according to claim 9, further comprising the step of utilizing a filter to enhance the contrast of the image in the discrete regions.

11. The method according to claim 10, wherein the article comprises an absorbent article.

12. The method according to claim 11, wherein the absorbent article comprises a permeable topsheet and an impermeable backsheet having a pad core disposed between the topsheet and the backsheet.

13. The method according to claim 12, wherein the absorbent article further comprises a pair of wings that extend laterally from longitudinal sides of the pad core, the wings having outer edges and being folded over the pad core such that the outer edges of the wings are adjacent each other.

14. The method according to claim 13, further comprising the step of determining the alignment of the overlaying edges of the wings and comparing the alignment to the skew of the article.

15. A process for inspecting an absorbent article using a camera and an image analyzer, constructed from multiple components including at least a permeable topsheet, an impermeable backsheet, and a pad core disposed between the topsheet and the backsheet, the process comprising:
    producing an image from the absorbent article;
    filtering the image of the absorbent article;
    identifying in the image of the absorbent article, a nonlinear first edge wherein the first edge is a location where there is a coarse change in contrast;
    identifying in the image of the absorbent article, a second edge wherein the second edge is a location where there is a coarse change in contrast;
    calculating a center point of the absorbent article using the position of the first edge and the second edge;
    determining a centerline of the absorbent article;
    calculating a skew of the absorbent article;
    utilizing at least one of the first edge, the second edge, the center point, or the centerline to define at least one region of the image for further analysis;
    utilizing a filter to enhance the contrast of the image in the defined region;
    identifying in the defined region, a third edge wherein the third edge is a location where there is a fine change in contrast;
    identifying in the defined region, a fourth edge wherein the fourth edge is a location where there in is a fine change in contrast;
    calculating the skew of the third edge and the fourth edge within the defined region; and
    comparing the skew of the third edge and the fourth edge to known parameters for the absorbent article.

* * * * *